United States Patent [19]

Fogarty et al.

[11] Patent Number: 5,234,425

[45] Date of Patent: Aug. 10, 1993

[54] VARIABLE DIAMETER SHEATH METHOD AND APPARATUS FOR USE IN BODY PASSAGES

[75] Inventors: Thomas J. Fogarty, Portola Valley; George D. Hermann, Los Gatos; Albert K. Chin, Palo Alto, all of Calif.

[73] Assignee: Thomas J. Fogarty, Portola Valley, Calif.

[21] Appl. No.: 982,032

[22] Filed: Nov. 24, 1992

Related U.S. Application Data

[63] Continuation of Ser. No. 614,865, Nov. 16, 1990, abandoned, which is a continuation-in-part of Ser. No. 319,521, Mar. 3, 1989, abandoned.

[51] Int. Cl.5 .............................................. A61B 17/00
[52] U.S. Cl. ........................................ 606/1; 606/198
[58] Field of Search .............. 606/106, 108, 109, 127, 606/128, 152, 153, 156, 198, 200, 201, 151, 1; 604/104, 280

[56] References Cited

U.S. PATENT DOCUMENTS

| | | | |
|---|---|---|---|
| 2,230,226 | 2/1941 | Auzin | 128/349 |
| 4,243,040 | 1/1981 | Beecher | 128/328 |
| 4,315,512 | 2/1982 | Fogarty | 128/344 |
| 4,469,100 | 9/1984 | Hardwick | 128/328 |
| 4,493,711 | 1/1985 | Chin et al. | 604/271 |
| 4,572,186 | 2/1986 | Gould et al. | 128/341 |
| 4,597,389 | 7/1986 | Ibrahim et al. | 128/328 |
| 4,655,771 | 4/1987 | Wallsten | 623/1 |
| 4,706,671 | 11/1987 | Weinrib | 128/348 |
| 4,776,337 | 10/1988 | Palmaz | 128/343 |

FOREIGN PATENT DOCUMENTS

| | | |
|---|---|---|
| 1566147 | 10/1967 | Fed. Rep. of Germany . |
| 1935856 | 7/1969 | Fed. Rep. of Germany . |
| 2945237 | 11/1979 | Fed. Rep. of Germany . |
| 3100144 | 1/1981 | Fed. Rep. of Germany . |
| 0169784 | 7/1985 | France . |
| WO8607267 | 6/1986 | PCT Int'l Appl. . |

Primary Examiner—Michael H. Thaler
Attorney, Agent, or Firm—Limbach & Limbach

[57] ABSTRACT

A tubular sheath capable of assuming a reduced diameter state for insertion into a body passage and of expanding once in place within the passage. The sheath is fabricated of a composite elastomeric material and axially stretched to assume the reduced diameter state. Selective axial stretching is achieved by an elongate stylet which extends slidably through the sheath for compression imparting engagement with a distal portion thereof.

21 Claims, 2 Drawing Sheets

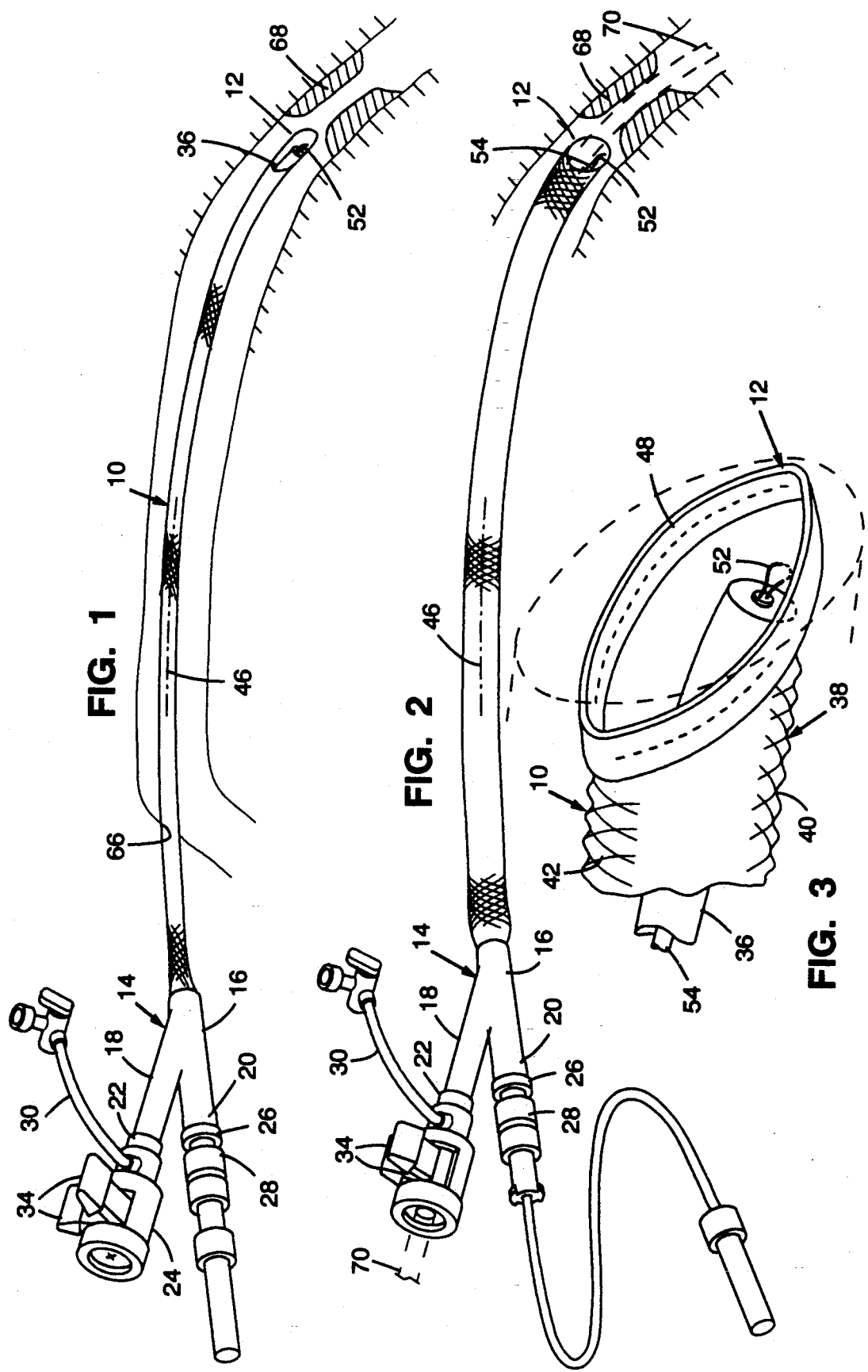

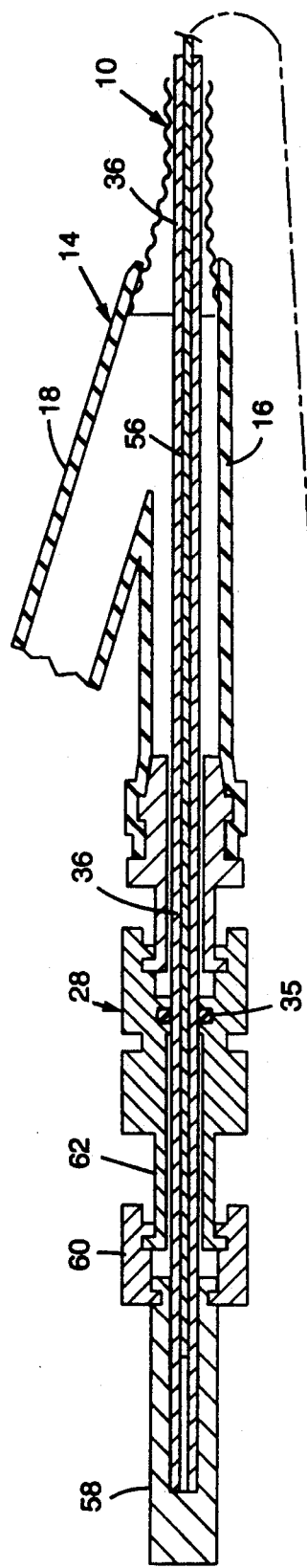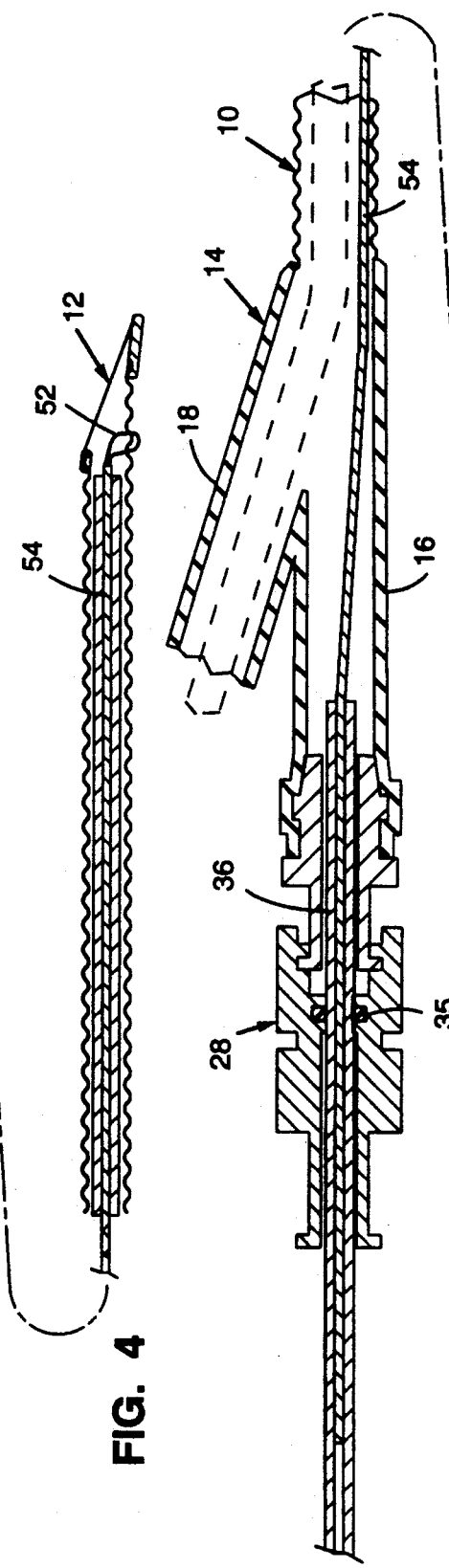

VARIABLE DIAMETER SHEATH METHOD AND APPARATUS FOR USE IN BODY PASSAGES

RELATED APPLICATION

This is a continuation of co-pending application Ser. No. 07/614,865 filed on Nov. 16, 1990, now abandoned, which in turn is a continuation-in-part of application Ser. No. 319,521 filed on Mar. 3, 1989, now abandoned.

FIELD OF THE INVENTION

The present invention relates to a method and apparatus for placing a sheath within a body passage and, more particularly, is concerned with such a method and apparatus for inserting a sheath into a blood vessel. In its more specific aspects, the invention is concerned with a method and apparatus wherein the sheath is surgically or percutaneously inserted into a blood vessel in a reduced-diameter state and, once within the vessel, expanded to the full interior diameter of the vessel.

DISCUSSION OF THE RELATED ART

In vascular applications, sheaths provide a temporary pathway to the interior of an artery or vein. This pathway facilitates the placement and removal of various instruments by protecting the adjacent tissue, vessel and puncture site. These sheaths often contain a hemostasis valve to prevent leakage of blood out of the proximal end of the sheath. A sideport is often included as well, to provide fluid access for such tasks as infusion of anticoagulants and contrast media.

The most common sheath design for vascular use presently in use is a simple thin-walled tube made of a non-distensible plastic material (e.g. Teflon). Such sheaths are of a fixed diameter and in the larger sizes are relatively inflexible. There have also been efforts to provide non-distensible sheaths which are highly flexible. U.S. Pat. No. 4,493,711 shows such a construction wherein the sheath is a very thin membrane which is originally inverted within the end of a catheter and, upon reaching the desired situs, everted from the catheter.

The prior art also teaches the concept of distending the balloon of a dilatation catheter in order to reduce its cross-section for placement within a blood vessel. U.S. Pat. No. 4,315,512 by Thomas J. Fogarty, one of the co-inventors herein, discloses such a catheter. In the case of that catheter, however, the distended balloon does not provide a pathway sheath to facilitate the placement of other instruments, or the removal of occlusions.

SUMMARY OF THE INVENTION

The principal component of the sheath comprises an elongate elastomeric tubular body having an outside diameter substantially equal to that of the body passage within which it is to be received. The tubular body has an open distal end. Contraction means is provided to stretch and laterally contract the body.

The invention provides a method of lining a body passage, such as a blood vessel, with a thin-walled single thickness interior sheath. The first step of the method comprises providing an elongate elastomeric tube having an open distal end and a generally uniform outside diameter substantially equal to that of the passage. In practice of the method, the tube is distended to reduce its outside diameter to less than that of the body passage. The tube is then threaded into the body passage while in the distended condition. Once at the desired location within the passage, the tube is relaxed from distension to permit it to expand to form a sheath in contact with the interior of the passage.

A principal object of the invention is to provide a flexible variable diameter sheath which may be inserted into a body passage in a reduced diameter condition and, once in place, expanded to the full size of the passage to seal thereagainst.

Another object of the invention is to provide such a sheath which is of thin-walled single thickness construction.

Still another object of the invention is to provide such a sheath which may be surgically or percutaneously inserted into a blood vessel in the reduced-diameter state and, once within the vessel, expanded to several times its reduced-diameter state.

Yet another object of the invention is to provide such a sheath which is fabricated of an elastomeric material and may be reduced in diameter by distension.

Yet another object related to the latter object, is to provide such a sheath wherein, when in a passive state, the sheath assumes the expanded-diameter condition.

Still another object related to the latter object is to provide such a sheath which is expandable to accommodate the passage of an oversized object therethrough.

Another and more general object is to provide such a sheath which is highly flexible so that it may conform to the shape of tortuous body passages through which it is threaded.

Still another and more general object of the invention is to provide such a sheath which may be percutaneously or surgically inserted in a reduced-diameter state to minimize the size of the percutaneous puncture or the incision and the force required for insertion of the sheath.

A further object of the invention is to provide a sheath for use in a blood vessel to shield the interior of the vessel against abrasion by instruments passed therethrough.

Another object of the invention related to the latter object is to provide such a sheath with a Y-branch inlet which enables the sheath to be simultaneously used for multiple purposes.

Still another object of the invention related to the latter object is to incorporate into the Y-branch a mechanism for stretching the sheath to reduce its diameter.

Yet another object related to the latter object is to provide such a mechanism wherein stop means is provided to control and limit the degree of stretching of the sheath.

Still another object of the invention is to provide such a sheath which has a highly pliable distal end to facilitate its introduction into and passage through a body passage.

Still a further and more specific object of the invention is to provide a distension means for such a sheath which takes the form of a wire extending through the sheath and secured to its distal end and a thin tubular stylet which may be extended over the wire to impart stretching force to the sheath.

These and other objects will become more apparent when viewed in conjunction with the following detailed description and accompanying drawings.

BRIEF DESCRIPTION OF THE DRAWINGS

FIG. 1 is a perspective view of the sheath in the process of being introduced into a blood vessel, with the sheath in a distended reduced diameter condition.

FIG. 2 is a perspective view similar to FIG. 1, illustrating the sheath in a relaxed expanded condition within the vessel, with phantom lines showing an instrument which has been passed through the sheath and into an occluded area of the vessel;

FIG. 3 is an enlarged perspective view of the sheath, with parts thereof broken away, illustrating the pliable distal end which is provided on the sheath;

FIG. 4 is a cross-sectional elevational view of the sheath, with parts thereof broken away, illustrating the sheath in the distended reduced diameter condition and the internal construction of the hub which is provided for extending the distension stylet through the sheath; and, FIG. 5 is a cross-sectional elevational view similar to FIG. 4, illustrating the sheath in the expanded condition and the Y-hub being used to introduce an instrument through the sheath.

DESCRIPTION OF THE PREFERRED EMBODIMENTS

Referring now to FIG. 1, the sheath is designated therein in its entirety by the numeral 10. The sheath is elongate and proportioned to expand, when relaxed, to an outside diameter approximately equal to the inside diameter of the body passage within which the sheath is to be used. As shown in the example of FIG. 1, the body passage comprises an artery 11. In a typical embodiment for vascular use, the sheath has an expanded "relaxed" diameter of from 6 to 7 mm, a contracted reduced diameter of 2 to 3 mm and a length of from 15 to 30 cm. The distal end of the sheath, designated 12, extends obliquely to the longitudinal axis of the sheath. The proximal end of the sheath is open and sealingly secured to the interior of a Y-shaped hemostasis hub 14. The hub 14 is tubular and has a primary leg 16 secured in sealed fluid communication to the interior of the sheath 10 and secondary legs 18 and 20 merging into communication with the primary leg. The free end of the secondary leg 18 carries an externally threaded coupling 22 for receipt of a hemostasis valve 24. The free end of the secondary leg 20 carries an externally threaded coupling 26 for receipt of a hemostasis valve 28.

In the embodiment illustrated, the valve 24 is of the type shown in copending application Ser. No. 429,854, filed Oct. 31, 1989. This type of valve may be selectively sealed, or opened to permit elongate objects to be slid therethrough and into the sheath. It may also be provided with a sideport tube 30 secured in sealed fluid communication with the interior of the valve, which sideport tube is provided with a conventional stopcock 32. Levers 34 forming part of the valve 24 cooperate with a seal within the valve to normally close the valve and, when compressed toward one another, open the valve for the passage of elongate elements therethrough.

The valve 28 carries a seal 35 (see FIG. 4) for sealed slidable engagement with a flexible tubular stylet 36 extended therethrough.

The internal construction of the preferred embodiment of the sheath 10 comprises a tubular braid 38 encapsulated within a coating 40 of high-elongation silicone polymer to provide an impermeable body 41. The braid is a woven structure of flexible generally inelastic polyester monofilaments 42, such as Dacron. While the proportions of the sheath may vary, depending upon the size and type of body passage within which it is intended to be used, the following is a typical example for arterial use:

| | |
|---|---|
| Tubular Sheath Body 41: | 30 cm long and 6 mm OD in relaxed condition; 37 cm long and 3 mm OD in axially distended contracted condition |
| Wall Thickness of Tubular Sheath Body 41: | 0.50 mm |
| Braid 38: | 6 mil. polyester monofilament manufactured by Atkins Pearce Manufacturing of Covington, Kentucky under No. GP-4819425 |
| Coating 34: | High elongation silicone elastomer manufactured by Dow Corning of Midland, Michigan under No. Q7-2213 |

In this example, the filaments 42 extend at an angle $\alpha$ of approximately 35°–50° relative to the longitudinal axis, designated 46, of the sheath when the sheath is in the relaxed expanded condition. In the distended contracted condition (see FIG. 1) the filaments extend at an angle $\beta$ of approximately 20° relative to the longitudinal axis 46 of the sheath.

The filaments 42 and their angular relationship relative to the longitudinal axis 46 both reinforce the elastomeric coating 40 and facilitate contraction and expansion of the sheath. The filaments also serve to control expansion, contraction and the elongation of the sheath.

The distal end 12 extends at an oblique angle relative to the axis 46. This angle is chosen so as to increase the area of the open distal end and to provide a gentler taper to facilitate introduction, as compared to what would occur if the angle were 90°. In the preferred embodiment, the angle is chosen so as to be approximately equal to the angle $\alpha$ so that the distal most filaments run generally parallel to the distal edge. The edge of the distal end 12 is bounded by an extension 48 of highly pliable elastomeric material corresponding to that of the coating 40. This extension facilitates guiding of the sheath into place and minimizes the possibility that the end of the sheath will serve to abrade the interior of a body passage within which the sheath is received.

Elongation of the sheath to contract its tubular body is provided by extending the stylet 36 through the sheath to a compression-imparting connection adjacent the distal end 12. In the preferred embodiment, the stylet 36 is tubular and secured adjacent the distal end 12 by a wire 52 which loops through the sidewall of the sheath and around a filament therein and is folded upon itself and received within a fine flexible tube 54. The wire 52 is ideally a corrosion resistant material of high tensile strength, such as stainless steel. The tube 54 is made of a highly flexible material capable of being fabricated into a thin wall and having a low coefficient of friction, such as polyimide.

The stylet 36 is fabricated of a highly flexible generally incompressible material, such as polyurethane. It is formed with a bore 56 proportioned for slidable extension over the tube 54. The tube 54, with the folded wire 52 therein, extends through the full length of the sheath 10 and from the proximal end thereof through the leg 20 of the hub 14. In the extended condition shown in FIG. 4, the stylet 36 is slidably received on the tube 54 and also extends through the full length of the sheath 10 and from the leg 20 of the hub 14.

The proximal end of the stylet 36 has a handle 58 fixedly secured thereto (see FIG. 4) which rotatably carries an internally threaded nut 60 engagable with an externally threaded extension 62 on the valve 28. When threadably engaged (see FIG. 4) the nut 60 and extension 62 serve to secure the stylet in the condition extending the sheath to the contracted condition and also serve as stop means to limit the extent of such extension. When disengaged, the nut and extension permit the stylet to be retracted from the sheath, thus relaxing the sheath for expansion. In the latter condition, the stylet may be fully withdrawn from the sheath (see FIG. 5), thus leaving the sheath in a condition of maximum flexibility with the passage therein substantially unobstructed, except for the presence of the tube 54.

In use, the hub 14 serves as a grip to restrain the proximal portion of the sheath against movement as the distal end is longitudinally extended by the stylet 36. FIG. 1 shows the sheath 10 in the process of being introduced into the artery 11 through a percutaneous puncture 66 providing a point of ingress into the artery. Although percutaneous insertion is shown in the illustration, it should be understood that insertion might also be provided surgically through an incision made in the artery. FIGS. 1 and 2 also show a stenosis 68 within the artery 11 at a location remote from the point of ingress 66. From FIG. 1, it will be seen that the sheath 10 is of a length sufficient to extend from the point of ingress 66 to the stenosis 68, thereby enabling the sheath to be used to direct instruments, such as dilatation catheters, through the sheath and into treating relationship to the stenosis.

In the condition shown in FIG. 1, the stylet 36 has been distended by engagement of the nut 60 with the extension 62, thus fully contracting the external diameter of the stylet for insertion into the artery. Once fully in place within the artery, as shown in FIG. 2, the nut 60 is disengaged from the extension 62 and the stylet is withdrawn, thus permitting the sheath to fully expand within the artery and removing the stylet from the interior of the sheath. In the latter condition, the interior of the sheath is unobstructed, except for the presence of the tube 54.

With the sheath fully in place as shown in FIG. 2, a dilatation catheter, or other desired instrument, may be extended through the hemostasis valve 24 and the full length of the sheath 10. The valve 24 may be selectively opened to accommodate such extension. The phantom lines shown in FIG. 2 illustrate a dilatation catheter 70 extended fully through the sheath and out of the distal end thereof into treating relationship to the stenosis 68.

It should be appreciated that the sheath may be left in place within the artery and that instruments may be traversed back and forth through the sheath without abrading the internal surfaces of the artery. When the desired treatment is complete, the instrument, such as the dilatation catheter 70, is removed from the sheath and the sheath is once again distended to the contracted condition, as shown in FIG. 1. Then, the sheath may be withdrawn from the artery in the reduced diameter condition, with a minimum of abrasion or disturbance to the wall of the artery.

In addition to providing for the introduction of instruments into the artery, the sheath may also be used for purposes of taking pressure measurements, or making injections. The sideport tube 30 may be used for such purposes.

CONCLUSION

While a preferred embodiment of the invention has been illustrated and described, it should be understood that the invention is not intended to be limited to this embodiment, but rather is defined by the accompanying claims.

We claim:

1. A variable diameter sheath for insertion into a body passage from a point of ingress to the passage, said sheath comprising:
   a) a flexible tubular body of a generally uniform outside diameter insertable into the body passage through the point of ingress, said tubular body being elongate and pliable to conform to the shape of the body passage and having:
      (1) an open proximal end fixedly secured to a hub and a free open and unobstructed distal end;
      (2) an elongate portion extending from the hub to the free open distal end, which elongate portion is expansible to a relaxed outside diameter substantially equal to that of the passage, said elongate portion being: of a length sufficient to extend from and through the point of ingress to an area within said passage remote from the point of ingress; and formed by a thin self-supporting wall which serves to shield the passage from internal abrasion by objects passed through the sheath;
   (b) contraction means incorporated into the tubular body to diametrically contract the elongate portion while in the body passage responsive to axial distension of said portion; and,
   (c) motion imparting means to selectively axially distend the elongate portion while in the body passage.

2. A sheath according to claim 1 wherein said contraction means is adapted to:
   (a) diametrically expand the elongate portion to a diameter substantially equal to that of the body passage in response to axial contraction of the portion by the motion imparting means; and,
   (b) diametrically contract said portion to a diameter substantially less than that of said body passage in response to axial distension of the portion by the motion imparting means.

3. A sheath according to claim 1 wherein the contraction means is adapted to diametrically contract the elongate portion by substantially one-half or more in response to axial distension by said motion imparting means.

4. A sheath according to claim 1 wherein the motion imparting means comprises:
   (a) an elongate generally incompressible element extending along the tubular body for longitudinal movement relative thereto; and,
   (b) connecting means adapted to secure said element in compression imparting relationship to the body adjacent the open distal end thereof.

5. A sheath according to claim 4 wherein the elongate element extends over the full length of the tubular body and from the open proximal end thereof, said sheath further comprising grip means on the elongate element for manual gripping to impart compressive force to the element.

6. A sheath according to claim 5 wherein the hub comprises a tubular Y-shaped fitting, said fitting having a primary leg secured in communication with the open proximal end of the tubular body and secondary legs merging into communication with said primary leg, said elongate element extending from the open proximal end of the tubular body through the fitting.

7. A sheath according to claim 6 further comprising mutually engagable stop means on the elongate element and the fitting to limit the extent to which the elongate element can be extended relative to the tubular body.

8. A sheath according to claim 7 further comprising lock means to secure the mutually engagable stop means in an engaged condition.

9. A sheath according to claim 6 wherein the elongate element extends through one of the secondary legs of the fitting and wherein the sheath further comprises:
  (a) seal means on said one leg establishing a fluid tight seal between the fitting and the elongate element, while permitting movement of the element relative to the fitting; and,
  (b) valve means on the other of said secondary legs to close said other leg against fluid flow, while permitting instruments to be passed therethrough.

10. A sheath according to claim 4 wherein:
  (a) the elongate element comprises a tubular stylet extending longitudinally through the tubular body; and,
  (b) the connecting means comprises a wire extending slidably through the stylet and secured to the body adjacent the open distal end thereof.

11. A sheath according to claim 1 wherein the tubular body is elastomeric and the contraction means comprises a plurality of intersecting flexible generally inelastic filaments incorporated into the body, said filaments extending obliquely to the longitudinal axis of the body.

12. An elongate variable diameter sheath for insertion into a body passage from a point of ingress to the passage, said sheath comprising:
  (a) an impermeable elastomeric tubular body, said body being: insertable into the body passage through the point of ingress, elongate and pliable to conform to the shape of the body passage and having:
    (1) an open proximal end fixedly secured to a hub and a free open and unobstructed distal end;
    (2) an elongate portion extending from the hub to the free open distal end, which elongate portion has a longitudinal axis and is expansible to a relaxed outside diameter substantially equal to that of the passage, said elongate portion being: of a length sufficient to extend from and through the point of ingress to an area within said passage remote from the point of ingress; and formed by a thin self-supporting wall which serves to shield the passage from internal abrasion by objects passed through the sheath;
  (b) intersecting flexible generally inelastic filaments incorporated into the body and extending obliquely of the longitudinal axis of the elongate portion to diametrically contract the elongate portion while in the body passage responsive to axial distension of said portion; and,
  (c) motion imparting means to selectively axially distend the elongate portion and axially contract said portion while in the body passage.

13. A sheath according to claim 12 wherein the motion imparting means comprises:
  (a) an elongate generally incompressible element extending along the body for longitudinal movement relative thereto; and,
  (b) connecting means adapted to secure said element in compression imparting relationship to the body adjacent the open distal end thereof.

14. A sheath according to claim 13 wherein said elongate element extends from the open proximal end of the tubular body through the hub and further comprising mutually engageable stop means on the elongate element and the hub to limit the extent to which the elongate element can be extended relative to the tubular body.

15. A sheath according to claim 14 further comprising lock means to secure the mutually engagable stop means in an engaged condition.

16. A sheath according to claim 14 wherein:
  (a) the hub is Y-shaped and has a primary leg secured in communication with the open proximal end of the tubular body and secondary legs merging into communication with the primary leg and wherein the elongate element extends through one of the secondary legs of the hub; and,
  (b) the sheath further comprises:
    (1) seal means on said one leg establishing a fluid tight seal between the hub and the elongate element, while permitting movement of the element relative to the hub; and,
    (2) valve means on the other of said secondary legs to close said other leg against fluid flow, while permitting instruments to be passed therethrough.

17. A sheath according to claim 13 wherein the elongate element extends over the full length of the tubular body, further comprising grip means on said element for manual gripping to impart compressive force to the element.

18. A sheath according to claim 13 wherein:
  (a) the elongate element comprises a tubular stylet extending longitudinally through the sheath; and,
  (b) the connecting means comprises a wire extending slidably through the stylet and secured to the body adjacent the open distal end thereof.

19. A sheath according to claim 12 wherein the open distal and extends obliquely to the longitudinal axis of the elongate portion and is bounded by a pliable elastomeric extension.

20. A method of lining a body passage from a point of ingress into the passage to an area within the passage remote from said point, said method comprising:
  (a) providing a pliable elongate single thickness elastomeric tube having:
    (1) an open proximal end fixedly secured to a hub and a free open and unobstructed distal end;
    (2) an elongate portion extending from the hub to the free open distal end, which elongate portion is expansible to a relaxed outside diameter substantially equal to that of the passage, said elongate portion being of a length sufficient to extend from and through the point of ingress to said area remote from said point;

(b) axially distending said tube to diametrically contract the elongate portion to a diameter less than that of the passage;

(c) threading the tube through the point of ingress and into the body passage while the elongate portion is axially distended; and, (d) relaxing the tube from axial distension to permit the elongate portion to diametrically expand within the passage.

21. A method according to claim 20 wherein the tube is distended by:
   (a) extending an elongated stylet along the tube;
   (b) engaging the stylet with the tube closely adjacent the distal end thereof; and,
   (c) applying compressive force to the stylet while restraining the proximal end to stretch the tube.

* * * * *